US00PP09177P

United States Patent [19]

Hrebeniuk

[11] Patent Number: Plant 9,177

[45] Date of Patent: Jun. 20, 1995

[54] POINSETTIA PLANT NAMED 'H-327'

[76] Inventor: Alexander Hrebeniuk, R.D. #1, Box 118, Sugar Run, Pa. 18846

[21] Appl. No.: 257,102

[22] Filed: Jun. 8, 1994

[51] Int. Cl.[6] ..... A01H 5/00
[52] U.S. Cl. ..... Plt./86.4
[58] Field of Search ..... Plt. 86.4

*Primary Examiner*—Howard J. Locker

*Attorney, Agent, or Firm*—Webb Ziesenheim Bruening Logsdon Orkin & Hanson

[57] ABSTRACT

A poinsettia plant named H-327 particularly characterized by the combined characteristics of triple form, dark leaves, red non-fading bracts, and particularly its heat resistance. Plants are long lasting in shipment, greenhouse and home, and have upright and compact growth habit with free branching.

2 Drawing Sheets

BACKGROUND OF THE NEW PLANT

The present invention comprises a new and distinct cultivar of *Euphorbia pulcherrima* known by the varietal name H-327. The male parent of the new cultivar is Supjibi (U.S. Plant Pat. No. 6,592), and the female patent of the new cultivar is H-371, a proprietary selection from an old and no longer available commercial variety known as the C-1 family.

The new cultivar was discovered in November of 1990 in Sugar Run, Pa.; was first asexually reproduced by cuttings shortly thereafter in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Very resistant to heat when grown under black cloth and thus believed suitable in many climates.
2. Eight and one-half week response time under black cloth.
3. Six to eight uniformly spaced branches after centers and tops have been removed from cuttings, termed pinch.
4. May be grown from a single stem or from a pinched stem.
5. Bracts are oval and long pointed on single stem and pinched plant.
6. Foliage generally oval and long but on pinch plant some oak shaped.
7. Full bloom has three rows of bracts.
8. Stem is green to brownish-green.
9. The centers of the bloom are medium tight; cyathia are long lasting.
10. When grown from a single stem, many bracts form; 26 bracts have been observed on a fully developed bloom.
11. The plant spread is 14"–16" on a pinched stem and up to about 10" on a single non-pinched stem.
12. Bracts range in size from five (5) cm. to 15½ cm. long and 1½ cm. to 8½ cm. wide.
13. Under normal conditions the cultivar shows color by mid-October; the bracts are fully developed by mid-November and can be sold by Thanksgiving Day.
14. Because of medium growing height, there is no need to use the regulator cycocel. However, if cuttings are started too early, the plants do respond well to cycocel to retard growth.

15. Resistance to fade, excellent long-lasting and does well in shipment, greenhouse and the home.

This variety was tested in summertime heat under black cloth and compared with a number of other proprietary cultivars which are non-commercial and used for breeding purposes. This variety was the most heat resistant of all the varieties tested. In addition, this variety did not fade over time, making it very versatile.

DESCRIPTION OF THE DRAWINGS

The accompanying photographic drawing Sheet 1 illustrates the new cultivar, the color being as nearly true as possible with color illustrations of this type. Sheet 2 is a black and white photograph illustrating the plant's distinctive characteristics other than color.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight and one half week plants. The color readings were determined under natural light at 2:00 p.m. on Jan. 16, 1994 at Sugar Run, Pa. Color references are primarily to the R.H.S. Colour Chart of the Royal Horticultural Society of London.

The plant:

*Form.*—Triple.

*Growth habit.*—Compact; medium growth.

*Rooting.*—Very uniform and very fast.

*Blooming season.*—Eight and one-half weeks.

*Blooming habit.*—Large, long oval bracts on single stem; uprising on pinched plant; in triple rows; compact.

*Height.*—Up to 18 inches on single stem and 10–12 inches on pinched stem.

Foliage:

*Size.*—From 2½ cm. wide and 6½ cm. long, to 8 cm. wide and 15 cm. long.

*Quantity.*—Up to 16 leaves per stem depending on culture.

*Color.*—New foliage — Upper side, Yellow-Green Group 147 A. Under Side, Yellow-Green Group 147 B. Old foliage — Upper side, Yellow-Green Group 147 A. Under side, Yellow-Green Group 147 A. Leaf petiole — Greyed-Orange Group 177 A. Stem — Green Group 137 B. Upper stem Brownish-Green.

*Shape.*—Long; oval and pointed; on pinched plant some oak shaped.

*Texture.*—Upper side smooth. Under side rough because of veins.

*Edge of margin.*—Wavy.

*Disease resistance.*—Free of Botrytis.

Flower:

*Borne.*—Medium tight corymb.

*Quantity.*—Twelve to fourteen (12–14) cyathia.

*Color.*—Styles — Yellow-Green Group 145 A. Ovaries — Orange-Red Group 32 A. Pollen — Red-Purple Group 60 A.

*Stamens.*—Long lasting.

Bracts:

*Size.*—Immature 1½ cm. wide and 5 cm. long; fully grown 8½ cm. wide and 15½ cm. long.

*Veins.*—Midrib to margin; color Greyed-Orange Group 177 D.

*Quantity.*—Twenty-six (26) bracts.

*Color.*—Top, Red Group 46 C; Underside, Red Group 46 D. Petiole, Red Group 46 A.

I claim:

1. A new and distinct variety of poinsettia plant as herein shown and described, particularly characterized by its triple form, dark leaves, large bracts, heat resistance, non-fade and long lasting in shipment, greenhouse and home.

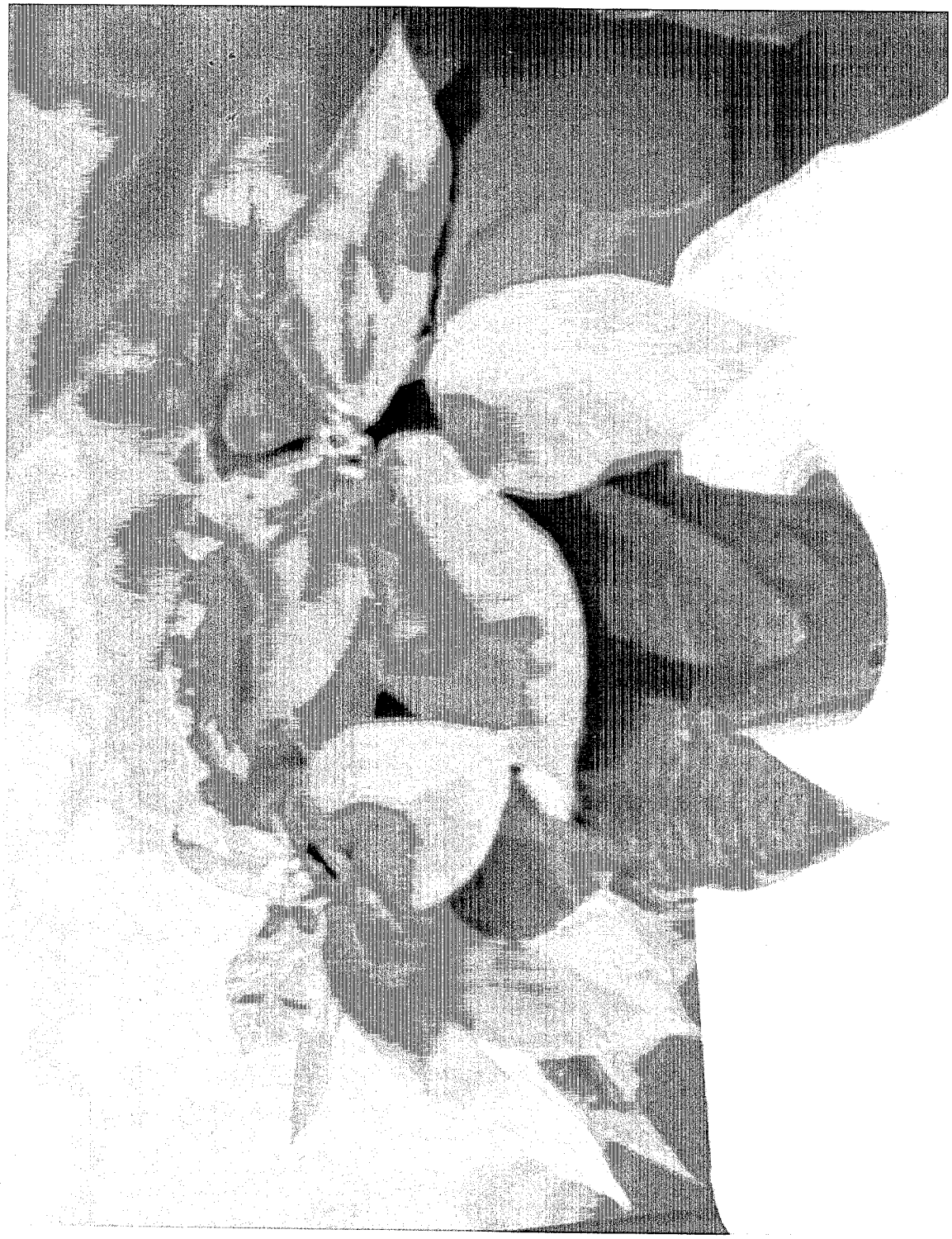

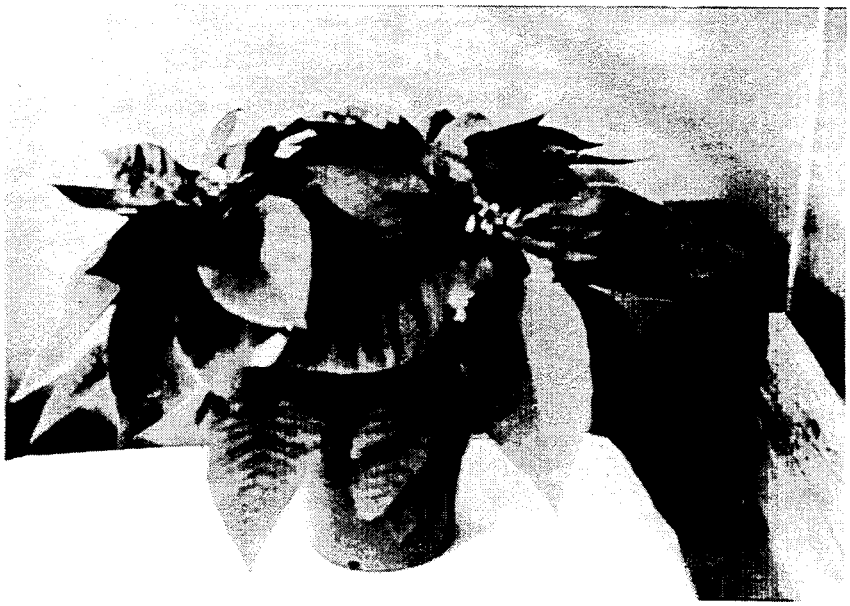

* * * * *